(12) United States Patent
Rehan et al.

(10) Patent No.: US 11,419,858 B2
(45) Date of Patent: Aug. 23, 2022

(54) COMPOSITION AND METHODS FOR TREATING HERITABLE PULMONARY ARTERY HYPERTENSION ASSOCIATED WITH NONSENSE MUTATIONS

(71) Applicant: The Lundquist Institute, Torrance, CA (US)

(72) Inventors: Virender K. Rehan, Torrance, CA (US); Terence M. Doherty, Corona, CA (US)

(73) Assignee: Lundquist Institute for Biomedical Innovation at Harbor-UCLA Medical Center, Torrance, CA (US)

( * ) Notice: Subject to any disclaimer, the term of this patent is extended or adjusted under 35 U.S.C. 154(b) by 53 days.

(21) Appl. No.: 16/800,152

(22) Filed: Feb. 25, 2020

(65) Prior Publication Data

US 2020/0268731 A1 Aug. 27, 2020

Related U.S. Application Data

(60) Provisional application No. 62/810,210, filed on Feb. 25, 2019.

(51) Int. Cl.
| | | |
|---|---|---|
| *A61K 31/4439* | (2006.01) | |
| *A61K 45/06* | (2006.01) | |
| *A61P 9/12* | (2006.01) | |
| *A61K 9/00* | (2006.01) | |

(52) U.S. Cl.
CPC ........ *A61K 31/4439* (2013.01); *A61K 9/0019* (2013.01); *A61K 9/0053* (2013.01); *A61K 9/0073* (2013.01); *A61K 45/06* (2013.01); *A61P 9/12* (2018.01)

(58) Field of Classification Search
CPC .................................................. A61K 31/4439
See application file for complete search history.

(56) References Cited

U.S. PATENT DOCUMENTS

| | | | | |
|---|---|---|---|---|
| 9,598,395 B2* | 3/2017 | Gatti | ........................ | A61P 25/00 |
| 2015/0051251 A1* | 2/2015 | Gatti | ........................ | A61P 25/00 |
| | | | | 514/333 |

OTHER PUBLICATIONS

Galie et al. CAS: 143: 432302, 2005.*

* cited by examiner

*Primary Examiner* — Rei Tsang Shiao
(74) *Attorney, Agent, or Firm* — Sheppard Mullin Richter & Hampton LLP

(57) ABSTRACT

The present disclosure relates generally to compositions and methods for treating, preventing, or slowing the rate of development of a disease or condition mediated by a nonsense mutation in the bone morphogenetic protein receptor type II (Bmpr2) in a subject in need thereof. The method entails administering to the subject a compound of the present disclosure, such as GJ103 and a salt thereof.

11 Claims, 4 Drawing Sheets

COMPOSITION AND METHODS FOR TREATING HERITABLE PULMONARY ARTERY HYPERTENSION ASSOCIATED WITH NONSENSE MUTATIONS

CROSS REFERENCE TO RELATED APPLICATIONS

This application claims the benefit under 35 U.S.C. § 119(e) of U.S. Provisional Application Ser. No. 62/810,210, filed Feb. 25, 2019, the content of which is incorporated by reference in its entirety into the present disclosure.

BACKGROUND

Inherited nonsense mutations cause or contribute to many diseases, most of which are catastrophic, lethal, or both. Nonsense mutations in a gene encode premature termination codons (PTCs) in their corresponding mRNA transcripts, which then cause synthesis of a truncated protein or no protein at all. If a truncated protein is produced, it is typically either nonfunctional, or rapidly degraded (usually both). Pulmonary artery hypertension (PAH) is a very deadly disease (5-year mortality after diagnosis is well over 50%). PAH is a generic designation for an array of specific diseases that have one thing in common: very high (sometimes over 100 mm Hg) blood pressure in the pulmonary arteries, which usually have quite low (~25 mm Hg or so) pressures. These high pressures eventually cause irreversible heart failure that leads to death. PAH can result from numerous causes, most of them acquired rather than inherited. Inherited (or possibly also acquired) nonsense mutations in the Bmpr2 gene are known to cause one specific form of PAH: heritable pulmonary artery hypertension (hPAH) in humans.

SUMMARY

A lead readthrough compound, GJ103, was identified as efficacious and safe in overcoming the nonsense mutations in the human BMPR2 gene, leading to increased expression and functional restoration of the BMPR2 protein. By contrast, another readthrough compound, G418 (an aminoglycoside antibiotic, also referred to as Geneticin and having the chemical name of (2R,3S,4R,5R,6S)-5-Amino-6-[(1R,2S,3S,4R,6S)-4,6-diamino-3-[(2R,3R,4R,5R)-3,5-dihydroxy-5-methyl-4-methylaminooxan-2-yl]oxy-2-hydroxycyclohexyl]oxy-2-(1-hydroxyethyl)oxane-3,4-diol), was unable to increase the expression of functional BMPR2 mRNA. Yet another readthrough compound, PTC-124 (Ataluren, with a chemical name of 3-[5-(2-Fluorophenyl)-1,2,4-oxadiazol-3-yl]benzoic acid), showed only modest increases. Both PTC-124 and G418 have been well-studied and considered promising therapeutic agents for diseases medicated by nonsense mutations. The identification of GJ103 as a lead and successful candidate for treating mutant BMPR2-mediated diseases, therefore, is surprising and unexpected.

In one embodiment, therefore, the present disclosure provides a method for treating, preventing, or slowing the rate of development of a disease or condition mediated by a nonsense mutation in the bone morphogenetic protein receptor type II (Bmpr2) in a subject in need thereof, comprising administering to the subject a compound of the present disclosure. In some embodiments, the compound is GJ103 or a salt thereof.

In some embodiments, the nonsense mutation decreases or eliminates the expression and activity of Bmpr2. Non-limiting examples include R584X, R321X, R899X and combinations thereof.

In some embodiments, the disease or condition is pulmonary artery hypertension (PAH), or pulmonary veno-occlusive disease (PVOD).

In some embodiments, the subject has the disease or condition. In some embodiments, the subject has the mutation and is at risk of developing the disease or condition.

Figure 1:
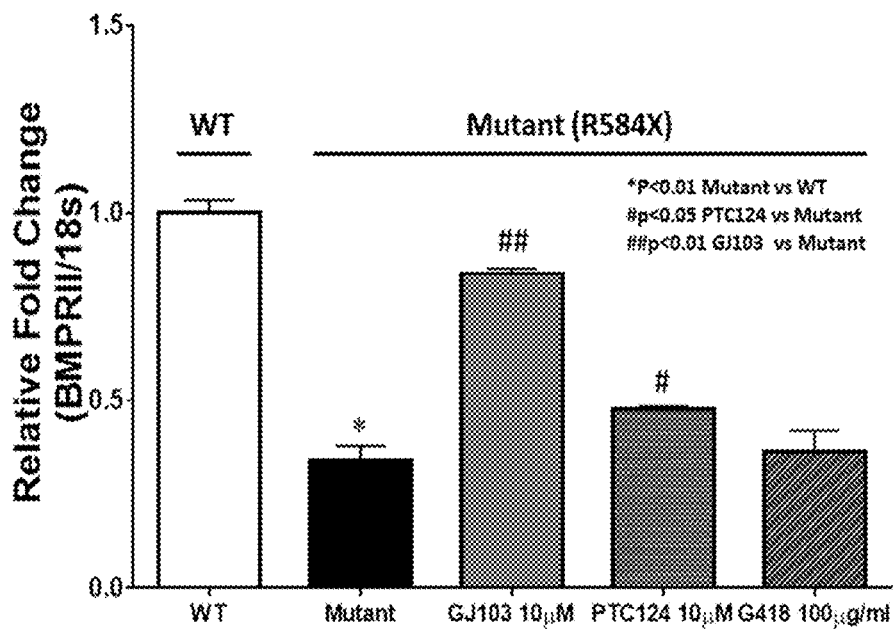
FIG. 1 shows that GJ103 increased mRNA expression levels in blood outgrowth endothelial cells (BOECs) from a patient with hPAH harboring a nonsense mutation (R584X) in the Bmpr2 gene (N=3). By contrast, two other tested readthrough compounds, PTC124 showed much less pronounced effect and G418 exhibited no effect.

It will be recognized that some or all of the figures are schematic representations for purpose of illustration.

DETAILED DESCRIPTION

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the con in which they are used indicates otherwise.

"Alkenyl" means a straight or branched hydrocarbon radical containing from 2-10 carbon atoms and at least one double bond, in another example 2-6 carbon atoms and one or two double bonds. Illustrative examples include, but are not limited to, allyl.

"Alkoxy" means an —OR group where R is alkyl, as defined herein. Illustrative examples include, but are not limited to, methoxy, ethoxy, propoxy, 2-propoxy, butoxy, tert-butoxy, pentyloxy, and hexyloxy.

"Alkoxyalkyl" means an alkyl group substituted with one or two alkoxy groups, as defined herein.

"Alkoxycarbonyl" means an alkoxy group, as defined herein, appended to the parent molecular moiety through a carbonyl group, as defined herein. Illustrative examples of alkoxycarbonyl include, but are not limited to, methoxycarbonyl, ethoxycarbonyl, and tert-butoxycarbonyl.

"Alkyl" means a straight or branched saturated hydrocarbon radical containing from 1-10 carbon atoms, in another example 1-6 carbon atoms. Illustrative examples include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl.

"Cycloalkyl" means a monocyclic or fused bicyclic, saturated or partially unsaturated, hydrocarbon radical of three to ten carbon ring atoms. Fused bicyclic hydrocarbon radical includes bridged rings. Unless stated otherwise, the valency of the group may be located on any atom of any ring within the radical, valency rules permitting. One or two ring carbon atoms may be replaced by a —C(O)—, —C(S)—, or —C(=NH)— group. Representative examples of cyclic include but are not limited to:

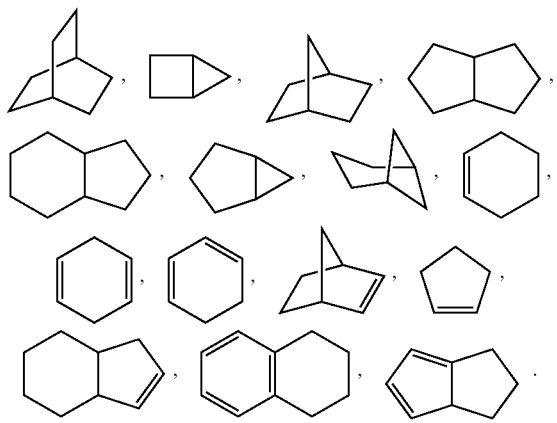

"Aryl" means a monovalent, monocyclic or fused bicyclic hydrocarbon radical of 6 to 12 ring atoms, wherein the ring comprising a monocyclic radical ring is aromatic and wherein at least one of the fused rings comprising a bicyclic radical is aromatic. Fused bicyclic hydrocarbon radical includes bridged ring systems. Unless otherwise stated, the valency of the group may be located on any atom of any ring within the radical, valency rules permitting. For example, the term aryl includes, but is not limited to, phenyl, naphthyl, indanyl (including, for example, indan-5-yl, or indan-2-yl, and the like) or tetrahydronaphthyl (including, for example, tetrahydronaphth-1-yl, or tetrahydronaphth-2-yl, and the like), and the like.

"Arylalkyl" means an alkyl group, as defined herein, substituted with one or two aryl groups as defined herein.

"Haloalkyl" means an alkyl group substituted with one or more halo atoms, in another example by 1, 2, 3, 4, 5, or 6 halo atoms, in another example by 1, 2, or 3 halo atoms. Examples include, but are not limited to, trifluoromethyl, chloromethyl, and the like.

"Heteroaryl" means monocyclic, fused bicyclic, or fused tricyclic, radical of 5 to 14 ring atoms containing one or more, in another example one, two, three, or four ring heteroatoms independently selected from —O—, —S(O)$_n$— (n is 0, 1, or 2), —N—, and —N(R$^{200}$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R$^{200}$ is hydrogen, alkyl, hydroxy, alkoxy, acyl, or alkylsulfonyl. Fused bicyclic radical includes bridged ring systems. Unless stated otherwise, the valency may be located on any atom of any ring of the heteroaryl group, valency rules permitting. In particular, when the point of valency is located on a nitrogen, R$^{200}$ is absent. The term heteroaryl includes, but is not limited to, 1,2,4-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), pyrazinyl, pyrimidinyl, pyridazinyl, oxazolyl, isooxazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, methylenedioxyphenyl (including, for example, methylenedioxyphen-5-yl), and the derivatives thereof, or N-oxide or a protected derivative thereof.

"Heteroarylalkyl" means an alkyl group, as defined herein, substituted with one or two heteroaryl groups, as defined herein.

"Heterocyclyl" means a saturated or partially unsaturated (but not aromatic) monocyclic group of 3 to 8 ring atoms or a saturated or partially unsaturated (but not aromatic) fused or bridged bicyclic or tricyclic group of 5 to 12 ring atoms in which one or more (specifically one, two, three, or four) ring atoms is a heteroatom independently selected from —O—, —S(O)$_n$— (n is 0, 1, or 2), —N=, and —NH— and the remaining ring atoms being carbon. One or two ring carbon atoms may be replaced by a —C(O)—, —C(S)—, or —C(=NH)— group. Unless otherwise stated, the valency of the group may be located on any atom of any ring within the radical, valency rules permitting. Illustrative examples include lactams, lactones, cyclic imides, cyclic thioimides, cyclic carbamates, More specifically the term heterocyclyl includes, but is not limited to, azetidinyl, pyrrolinyl, pyrrolidinyl, 2-oxopyrrolidinyl, 2,5-dioxo-1H-pyrrolyl, 2,5-dioxo-pyrrolidinyl, 2,5-dihydro-1H-pyrrolyl, piperidinyl, 4-piperidonyl, morpholinyl, piperazinyl, 2-oxopiperazinyl, dioxopiperazinyl, pyranyl, tetrahydropyranyl, tetrahydrothiopyranyl, 1,3-dioxinyl, 1,3-dioxanyl, 1,4-dioxinyl, 1,4-dioxanyl, 2-oxopiperidinyl, thiomorpholinyl, thiamorpholinyl, perhydroazepinyl, pyrazolidinyl, imidazolinyl, imidazolidinyl, 2,4-dioxo-imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, 1,3-oxathianyl, 1,4-oxathiinyl, 1,4-oxathianyl, tetrahydro-1,4-thiazinyl, 2H-1,2-oxazinyl, tetrahydrofuryl, 2,4,6-trioxo-(1H,3H,5H)pyrimidinyl, 4,6-dioxo-2-(1H,5H) thioxodihydropyrimidinyl, 2,4(1H,3H)-dioxo-dihydropyrimidinyl, trioxanyl, hexahydro-1,3,5-triazinyl, tetrahydrothienyl, tetrahydrofuranyl, pyrazolinyl, 1,3-dioxolyl, 1,3-dioxolanyl, 1,3-dithiolyl, 1,3-dithiolanyl, isoxazolinyl, isoxazolidinyl, oxazolidinonyl, 1,3-oxathiolanyl, 2(3H)-oxo-dihydrothienyl, 2(3H)-oxo-dihydrofuranyl, 1,1-dioxo-tetrahydrothienyl, 2-oxo-1,3-dioxolanyl, 4,5-dihydrooxazolyl, oxiranyl, (1s,4s)-7-oxabicyclo[2.2.1]heptanyl, 2,3-dihydrobenzo[b][1,4]dioxinyl, 4H-1,4-thiazinyl, octahydro-1H-quinolizinyl, and tetrahydropyranyl, and the derivatives thereof and N-oxide or a protected derivative thereof. Additional examples include

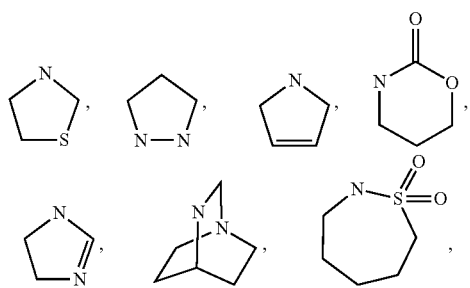

"Hydroxyalkyl" means an alkyl group, as defined herein, substituted with 1, 2, 3, or 4 hydroxy groups.

"Pseudohalo" means a cyano, cyanate (—N=C=O), thiocyanate group (—S=C=N), or azide.

"Thioalkoxy" means an —SR group where R is alkyl, as defined herein.

The terms "optional" or "optionally" means that the subsequently described event or circumstance may or may not occur and that the description includes instances where said event or circumstance occurs and instances in which it does not. Also, the term "optionally substituted" refers to any one or more (e.g., 1 to 5 or 1 to 3) hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one (e.g., 1 to 5 or 1 to 3) hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, —NHNH$_2$, =NNH$_2$, imino, imido, hydroxy, oxo, oxime, nitro, sulfonyl, sulfinyl, alkylsulfonyl, alkylsulfinyl, thiocyanate, —S(O)OH, —S(O)$_2$OH, sulfonamido, thiol, thioxo, N-oxide, or —Si(R$^y$)$_3$, wherein each R$^y$ is independently hydrogen, alkyl, alkenyl, alkynyl, heteroalkyl, cycloalkyl, aryl, heteroaryl, or heterocyclyl.

In certain embodiments, "substituted" includes any of the above alkyl, alkenyl, alkynyl, cycloalkyl, heterocyclyl, aryl, or heteroaryl groups in which one or more (e.g., 1 to 5 or 1 to 3) hydrogen atoms are independently replaced with deuterium, halo, cyano, nitro, azido, oxo, alkyl, alkenyl, alkynyl, haloalkyl, cycloalkyl, heterocyclyl, aryl, heteroaryl, —NR$^g$R$^h$, —NR$^g$C(O)R$^h$, —NR$^g$C(O)NR$^g$R$^h$, —NR$^g$C(O)OR$^h$, —NR$^g$S(O)$_{1-2}$R$^h$, —C(O)R$^g$, —C(O)OR$^g$, —OC(O)OR$^g$, —OC(O)R$^g$, —C(O)NR$^g$R$^h$, —OC(O)NR$^g$R$^h$, —OR$^g$, —SR$^g$, —S(O)R$^g$, —S(O)$_2$R$^g$, —OS(O)$_{1-2}$R$^g$, —S(O)$_{1-2}$OR$^g$, —NR$^g$S(O)$_{1-2}$NR$^g$R$^h$, =NSO$_2$R$^g$, =NOR$^g$, —S(O)$_{1-2}$NR$^g$R$^h$, —SF5, —SCF3, or —OCF3. In certain embodiments, "substituted" also means any of the above groups in which one or more (e.g., 1 to 5 or 1 to 3) hydrogen atoms are replaced with —C(O)R$^g$, —C(O)OR$^g$, —C(O)NR$^g$R$^h$, —CH$_2$SO$_2$R$^g$, or —CH$_2$SO$_2$NR$^g$R$^h$. In the foregoing, R$^g$ and R$^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. In certain embodiments, "substituted" also means any of the above groups in which one or more (e.g., 1 to 5 or 1 to 3) hydrogen atoms are replaced by a bond to an amino, cyano, hydroxy, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl, or two of R$^g$ and R$^h$ and R$^i$ are taken together with the atoms to which they are attached to form a heterocyclyl ring optionally substituted with oxo, halo, or alkyl optionally substituted with oxo, halo, amino, hydroxy, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein, is also intended to represent unlabeled forms as well as isotopically labeled forms of the compounds. These forms of compounds may also be referred to as "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Various isotopically labeled compounds of the present disclosure, for example those into which radioactive isotopes such as $^3$H and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life, reduced dosage requirements, and/or an improvement in therapeutic index. An $^{18}$F, $^3$H, $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino, and/or carboxyl groups, or groups similar thereto.

Provided are also or a pharmaceutically acceptable salt, isotopically enriched analog, deuterated analog, stereoisomer, mixture of stereoisomers, and prodrugs of the compounds described herein. "Pharmaceutically acceptable" or "physiologically acceptable" refer to compounds, salts, compositions, dosage forms, and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids, and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic or organic acids. Salts derived from inorganic acids include, e.g., hydrochloric acid, hydrobromic acid, sulfuric acid, nitric acid, phosphoric acid, and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic or organic bases. Salts derived from inorganic bases include, by way of example only, sodium, potassium, lithium, aluminum, ammonium, calcium, and magnesium salts. Salts derived from organic bases include, but are not limited to, salts of primary, secondary, and tertiary amines, such as alkyl amines (i.e., NH$_2$(alkyl)), dialkyl amines (i.e., HN(alkyl)$_2$), trialkyl amines (i.e., N(alkyl)$_3$), substituted alkyl amines (i.e., NH$_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., NH$_2$(alkenyl)), dialkenyl amines (i.e., HN(alkenyl)$_2$), trialkenyl amines (i.e., N(alkenyl)$_3$), substituted alkenyl amines (i.e., NH$_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., NH$_2$(cycloalkyl), HN(cycloalkyl)$_2$, N(cycloalkyl)$_3$), mono-, di- or tri-arylamines (i.e., NH$_2$(aryl), HN(aryl)$_2$, N(aryl)$_3$), or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine, and the like.

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds described herein, and the like. Preparation, selection, and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Treatment of Mutant BMPR2-Mediated Diseases

The present disclosure provides compositions and methods for treating diseases and conditions mediated by the human Bmpr2 gene with a mutation resulting in a premature termination codon (PTC). An example is the heritable pulmonary artery hypertension (hPAH) in humans. The methods, in some embodiments, employ a SMRT (Small Molecule Read-Through) compound that can read through the PTC in transcripts specified by the Bmpr2 gene. Such readthrough, as demonstrated herein, can markedly attenuate or even normalize high pulmonary artery pressures in those at risk of developing hPAH.

Currently, there are no effective therapies for this disease; all known treatments merely slow the inexorable rate of progression of the disease and forestall their inevitable lethality. PTC-124 (Ataluren, with a chemical name of 3-[5-(2-Fluorophenyl)-1,2,4-oxadiazol-3-yl]benzoic acid), for instance, was once a promising candidate SMRT, but the FDA rejected the new drug application twice, mostly based on lack of evidence for efficacy in Duchenne's muscular dystrophy.

In a surprising and unexpected discovery herein, GJ103 was identified as a lead compound, and was efficacious and safe in overcoming the nonsense mutations (R899X, R584X and R321X) in the human BMPR2 gene, leading to increased expression and functional restoration of the BMPR2 protein. By contrast, two well-known read-through compounds, G418 (Geneticin) and PTC-124 (PTC-124), were much less effective.

GJ103 has a chemical name of 2-((4-(3-methoxyphenyl)-5-(pyridin-2-yl)-4H-1,2,4-triazol-3-yl)thio)acetic acid, and can be used as a salt. The structures of GJ103 and a sodium salt are shown below.

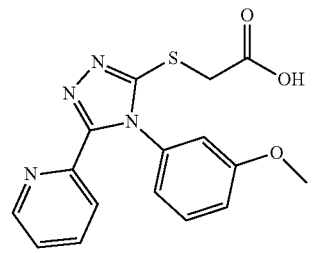 [SMILES: COc1cccc(-n2c(SCC(=O)O)nnc2-c2ccccn2)c1]

GJ103

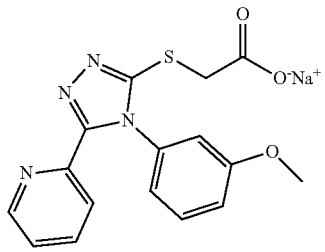

GJ103 salt

GJ103's effectiveness in treating hPAH was unexpected for at least the following reasons. First, SMRT compounds may or may not read through all PTCs in all genes. Second, even if a SMRT can read through a PTC, the rate at which the SMRT compound reads through the PTC might not be sufficient to overcome potential degradation of mutant mRNA transcripts caused by nonsense-mediated decay (NMD) mechanisms. Third, NMD might be so rapid and efficient that no mRNA transcripts stable enough to traffic to the ribosomes are produced. If mRNA transcript half-lives are too short, SMRT compounds would be completely ineffective. NMD efficiency and rapidity varies widely in different situations and diseases, and remains an empiric question for any one gene and transcript.

Fourth, even if a SMRT compound reads through a PTC in one or more of these genes efficiently and produce protein, that protein may or may not be functional. Fifth, SMRT compounds may or may not effect translation of sufficient quantities of protein to significantly impact the pathology caused by lack of one or more of these genes. Sixth, even if a functional protein is induced by a SMRT compound, it might still be ineffective. For example, it might not be possible to reverse the disease process underlying the pathology. Finally, a SMRT compound can insert a random amino acid at the PTC site. If the SMRT compound reads through PTCs in one or more of these genes efficiently, the protein produced will most likely contain an amino acid substitution at the site of the PTC, may therefore not fold into a correct three-dimensional conformation, and might therefore be nonfunctional and susceptible to degradation by the unfolded protein response. The success of GJ103, and its variants as disclosed herein, in the treatment of hPAH, therefore, is entirely surprising and unexpected.

In one embodiment, the present disclosure provides compositions and methods for treating or preventing a disease or condition mediated by a mutation in the bone morphogenetic protein receptor type II (Bmpr2). In some embodiments, the disease or condition is pulmonary artery hypertension (PAH). In some embodiments, the disease or condition is pulmonary veno-occlusive disease (PVOD).

Pulmonary arterial hypertension (PAH) is a condition characterized by abnormally high blood pressure (hypertension) in the blood vessel that carries blood from the heart to the lungs (the pulmonary artery). Many BMPR2 gene mutations can cause heritable PAH (hPAH). About half of the mutations involved in this condition disrupt the assembly of Bmpr2, reducing the amount of this protein in cells. Other mutations prevent bone morphogenetic protein receptor type 2 from reaching the cell surface or alter its structure so it cannot receive or transmit signals.

Pulmonary veno-occlusive disease (PVOD) is characterized by the blockage (occlusion) of the blood vessels that carry oxygen-rich (oxygenated) blood from the lungs to the heart (the pulmonary veins). The occlusion is caused by a buildup of abnormal fibrous tissue in the small veins in the lungs, which narrows the vessels and impairs blood flow. Bmpr2 mutations have been identified that cause heritable PVOD (hPVOD).

In some embodiments, the patient being treated has a nonsense mutation in the BMPR2 gene. Examples of such mutations include, without limitation, R584X, R321X, and R899X. In one embodiment, the patient has hPAH and has a R584X mutation. In one embodiment, the patient has hPAH and has a R321X mutation. In one embodiment, the patient has hPAH and has a R899X mutation.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition. The therapeutically effective amount may vary depending on the subject, and disease or condition being treated, the weight and age of the subject, the severity of the disease or condition, and the manner of administering, which can readily be determined by one or ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

In some embodiments, the composition includes a SMRT (Small Molecule Read-Through) compound, such as those disclosed herein. In one embodiment, the SMRT compound is a compound of Formula I, II or III, or a pharmaceutically acceptable salt, isotopically enriched analog, stereoisomer, mixture of stereoisomers, or prodrug thereof:

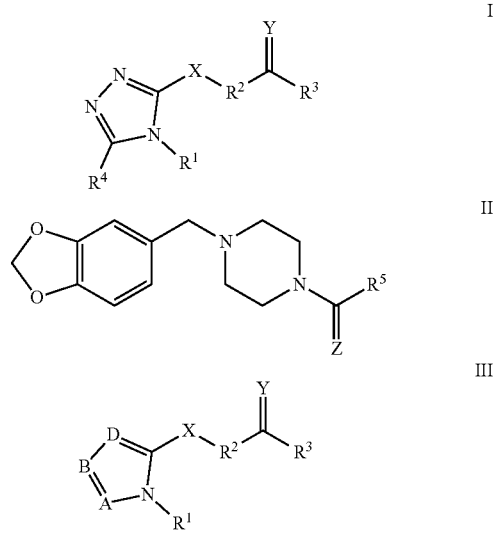

wherein:

X, Y, and Z are each independently O, S. or $NR^{10}$; wherein $R^{10}$ is hydrogen, alkyl, cycloalkyl, aryl, heterocyclyl or heteroaryl, where each alkyl, cycloalkyl, aryl, heterocyclyl or heteroaryl is independently optionally substituted;

A is N or $CR^{11}$; wherein $R^{11}$ is alkyl, cycloalkyl, aryl, heterocyclyl or heteroaryl, wherein each alkyl, cycloalkyl, aryl, heterocyclyl or heteroaryl, is independently optionally substituted;

B is N or CR$^{12}$; wherein R$^{12}$ is hydrogen, halo, pseudohalo, alkyl, alkoxy, or thioalkoxy;

D is N or CR$^{13}$; wherein R$^{13}$ is hydrogen, halo, pseudohalo, alkyl, alkoxy, or thioalkoxy;

R$^1$ is alkyl, cycloalkyl, aryl, heterocyclyl or heteroaryl, wherein each alkyl, cycloalkyl, aryl, heterocyclyl or heteroaryl is independently optionally substituted;

R$^2$ is C$_{1-3}$ alkylene, C$_{3-10}$cycloalkylene, or heterocyclylene of 3 to 10 atoms;

R$^3$ is hydroxy, alkoxy, —NR$^6$R$^{6a}$ alkyl, cycloalkyl, aryl, heterocyclyl or heteroaryl, wherein each alkyl, cycloalkyl, aryl, heterocyclyl or heteroaryl is independently optionally substituted;

R$^4$ is alkyl, cycloalkyl, aryl, heterocyclyl or heteroaryl, wherein each alkyl, cycloalkyl, aryl, heterocyclyl or heteroaryl is independently optionally substituted;

R$^5$ is —NR$^{5a}$R$^{5b}$, alkyl, cycloalkyl, aryl, heterocyclyl or heteroaryl, wherein each alkyl, cycloalkyl, aryl, heterocyclyl or heteroaryl is independently optionally substituted;

R$^{5a}$ is hydrogen or alkyl;

R$^{5b}$ is alkyl, alkoxyalkyl, alkenyl, aryl, arylalkyl, heteroaryl, or heteroarylalkyl; wherein the aryl or heteroaryl, either alone or as part of arylalkyl and heteroarylalkyl, are optionally substituted with 1, 2, or 3 groups independently selected from alkyl, halo, haloalkyl, hydroxy, and alkoxy;

R$^6$ is hydrogen or alkyl; and

R$^{6a}$ is —NHC(O)(arylalkyl), alkyl, hydroxyalkyl, cycloalkyl, heteroaryl, or aryl, wherein each aryl, arylalkyl, or heteroaryl are optionally substituted with 1, 2, or 3 groups selected from hydroxy, halo, haloalkyl, alkyl, alkoxy, carboxy, or alkoxycarbonyl.

In certain embodiments, the compound is a compound of Formula Ia, or a pharmaceutically acceptable salt, isotopically enriched analog, stereoisomer, mixture of stereoisomers, or prodrug thereof:

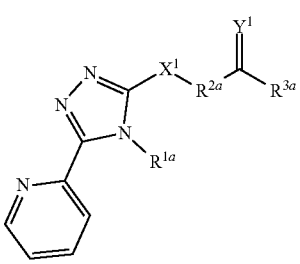

Ia wherein:

R$^{1a}$ is hydroxylphenyl, 2-alkoxyphenyl, 3-hydroxylphenyl, or 3-alkoxyphenyl;

X$^1$ is S, O, NH, or N(C$_{1-3}$-alkyl);

R$^{2a}$ is (CH$_2$)$_n$;

m is 1, 2, or 3;

Y$^1$ is O, S, or NH;

R$^{3a}$ is hydroxy or —NR$^7$R$^{7a}$;

R$^7$ is hydrogen or C$_{1-3}$-alkyl;

R$^{7a}$ is hydroxyalkyl; phenyl substituted with 1, 2, or 3 R$^8$ groups; phenyl substituted with two independently selected halo;

each R$^8$ is independently hydroxy or haloalkyl; and each R$^9$, when present, is independently hydroxy, alkoxy, halo, haloalkyl, or C$_{1-6}$-alkyl; and provided that 1) when X$^1$ is S, R$^{2a}$ is —CH$_2$—, Y$^1$ is O, and R$^{3a}$ is —NR$^7$R$^{7a}$ and R$^7$ is hydrogen, then R$^{7a}$ is not 2-methoxyphenyl; and 2) when R$^{1a}$ is 2-methoxyphenyl, X$^1$ is S, R$^{2a}$ is —CH$_2$—, Y$^1$ is O, and R$^{3a}$ is —NR$^7$R$^{7a}$ and R$^7$ is hydrogen, then R$_{7a}$ is not 4-methoxyphenyl.

In some embodiments, compounds of Formula I, II, III, Ia, and analogs or derivatives thereof, and methods of their synthesis, are described in U.S. Pat. No. 9,598,395, which is incorporated herein by reference.

In certain embodiments, the method utilizes a compound of formula:

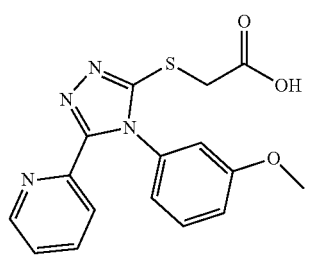 [SMILES: COc1cccc(-n2c(SCC(=O)O)nnc2-c2ccccn2)c1]

or a pharmaceutically acceptable salt, isotopically enriched analog, or prodrug thereof:

In certain embodiments, utilizes a compound of formula:

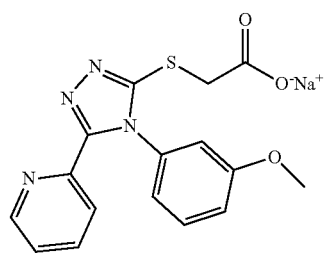

or an isotopically enriched analog, or prodrug thereof.

In come embodiments, the treatment or composition further includes a drug useful for treating PAH or PVOD. Examples of such drugs include, without limitation, ambrisentan (Letairis), bocentan (Tracleer), macitentan (Opsumit), riociguat (Adempas), selexipag (Uptravi), sildenafil (Revatio), tadalafil (Adcirca), treprostinil (Orenitram), Iloprost tromethamine (Ventavis), treprostinil (Tyvaso), epopostenol sodium (Flolan, Veletri), and treprostinil.

It is further contemplated that the co-administration of an agent that inhibits nonsense-mediated decay (NMD) can further enhance the therapeutic effect of the presently disclosed compounds. Abnormal transcripts such as those transcribed with a premature termination codon are generally detected by a cellular "housekeeping" system and targeted for degradation. It is contemplated that inhibiting this mechanism can enhance availability of mutant transcripts, which in turn favorably affect yield of the normal protein.

A RNA surveillance mechanism exists to minimize the translation and regulates the RNA stability of nonsense RNAs containing PTC mutations. This surveillance mechanism, referred to as "nonsense-mediated mRNA decay" ("NMD)," a post transcriptional mechanism that is operational in both normal cells (e.g., B and T cells) and cells with genetic mutations (i.e., cells with mutations in genes controlling cellular proliferation).

There are three main factors in NMD: UPF1, UPF2 and UPF3 (UPF3A and UPF3B in humans), that make up the conserved core of the NMD pathway. All three of these factors are trans-acting elements called up-frameshift (UPF)

proteins. In mammals, UPF2 and UPF3 are part of the "exon-exon junction complex" (EJC) bound to mRNA after splicing along with other proteins which also function in NMD. UPF1 phosphorylation is controlled by the proteins SMG-1, SMG-5, SMG-6 and SMG-7.

A NMD inhibitor may be an inhibitor of one or more proteins associated with the NMD degradation complex (such as, but not limited to, UPF1, UPF2, UPF3, eIF4AIII, MLN51, the Y14/MAGOH heterodimer, SMG-1, SMG-5, SMG-6 and/or SMG-7). As used herein, the phrase "NMD degradation complex" refers to any one of the intracellular proteins that participates in NMD of an mRNA bearing a PTC (such as, but not limited to, one or more of UPF1, UPF2, UPF3, UPF3BI, RNPS1, eIF4AIII, MLN51, the Y14/MAGOH heterodimer, RENT1, RENT2, SMG-1, SMG-5, SMG-6 and/or SMG-7). As such, the compound inhibits the function of one or more NMD degradation complex proteins, thereby allowing a PTC-bearing mRNA to be translated into a polypeptide.

Candidate compounds can be, without limitation, small molecule chemical compounds (such as any of the small molecules described above), antibodies, proteins, or any combination thereof. In one embodiment, the compound is not an inhibitory nucleic acid (such as, but not limited to, an antisense oligonucleotide or a small inhibitory RNA (siRNA)). In another embodiment, the compound is not any of the compounds disclosed in U.S. Patent Application Publication No. 2013/0224237.

In some aspects, the compound binds (such as preferentially binds) to a one or more NMD degradation complex proteins (such as, but not limited to, UPF1, UPF2, UPF3, UPF3BI, RNPS1, eIF4AIII, MLN51, the Y14/MAGOH heterodimer, RENT1, RENT2, SMG-1, SMG-5, SMG-6 and/or SMG-7) and is an antibody. In some embodiments, the antibodies are NMD degradation complex protein antagonists and can inhibit NMD.

In some aspects, the NMDI binds to a one or more NMD degradation complex proteins (such as, but not limited to, UPF1, UPF2, UPF3, UPF3BI, RNPS1, eIF4AIII, MLN51, the Y14/MAGOH heterodimer, RENT1, RENT2, SMG-1, SMG-5, SMG-6 and/or SMG-7) and is a non-antibody binding polypeptide. In some embodiments, the non-antibody binding polypeptide is a NMD degradation complex protein antagonist and can inhibit NMD.

Binding polypeptides may be identified without undue experimentation using well known techniques. In this regard, it is noted that techniques for screening polypeptide libraries for binding polypeptides that are capable of binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Application Publication Nos. WO 84/03506 and WO84/03564; Geysen et al, Proc. Natl. Acad. Sci. U.S.A., 81:3998-4002 (1984); Geysen et al, Proc. Natl. Acad. Sci. U.S.A., 82: 178-182 (1985); Geysen et al., J. Immunol. Meth, 102:259-274 (1987); Clackson, T. et al., (1991) Nature, 352: 624; Kang, A. S. et al., (1991) Proc. Natl. Acad. Sci. USA, 88:8363, and Smith, G. P. (1991) Current Opin. Biotechnol, 2:668, the disclosures of each of which are incorporated by reference herein.

Methods for generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323, the disclosures of each of which are incorporated by reference herein.

Binding polypeptides can be modified to enhance their inhibitory and/or therapeutic effect (including, for example, enhanced affinity, improved pharmacokinetic properties such as half-life, stability, and clearance rate, reduced toxicity, etc.). Such modifications include, without limitation, glycosylation, pegylation, substitution with non-naturally occurring but functionally equivalent amino acid, linking groups, etc.

Examples of NMDIs can include, for example, NMDI14, NMDI19 and/or NMDI25 or any other NMDI disclosed in Martin et al., (Cancer research, 2014, 74(11):3104-13) or in U.S. Patent Application Publication No. 2014/0094457, the disclosures of each of which are incorporated by reference herein.

Pharmaceutical Compositions and Modes of Administration

Compounds provided herein are usually administered in the form of pharmaceutical compositions. Thus, provided herein are also pharmaceutical compositions that contain one or more of the compounds described herein or a pharmaceutically acceptable salt, tautomer, stereoisomer, mixture of stereoisomers, prodrug, or deuterated analog thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, tautomer, stereoisomer, mixture of stereoisomers, prodrug, or deuterated analog thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, tautomer, stereoisomer, mixture of stereoisomers, prodrug, or deuterated analog thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, tautomer, stereoisomer, mixture of stereoisomers, prodrug, or deuterated analog thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1. GJ103 Increased Expression of BMPR2 mRNA and Protein Levels

Readthrough compounds such as PTC-124 and G418 (an aminoglycoside antibiotic) have shown significant increases in the expression of BMPR2 mRNA and protein in human cells containing the BMPR2 R899X nonsense mutation (data not shown).

This example sought to determine whether the readthrough compound GJ103 can achieve readthrough when treating blood outgrowth endothelial cells (BOECs) obtained from patients with hPAH caused by one of three distinct nonsense mutations in the BMPR2 gene (R899X, R584X and R321X).

Two other readthrough compounds, PTC-124 (Ataluren, with a chemical name of 3-[5-(2-Fluorophenyl)-1,2,4-oxadiazol-3-yl]benzoic acid) and G418 (an aminoglycoside antibiotic, also referred to as Geneticin and having a chemical name of (2R,3S,4R,5R,6S)-5-Amino-6-[(1R,2S,3S,4R,6S)-4,6-diamino-3-[(2R,3R,4R,5R)-3,5-dihydroxy-5-methyl-4-methylaminooxan-2-yl]oxy-2-hydroxycyclohexyl]oxy-2-(1-hydroxyethyl)oxane-3,4-diol), were used as references. Both PTC-124 and G418 have shown readthrough effectiveness in previous studies.

Figure 2:
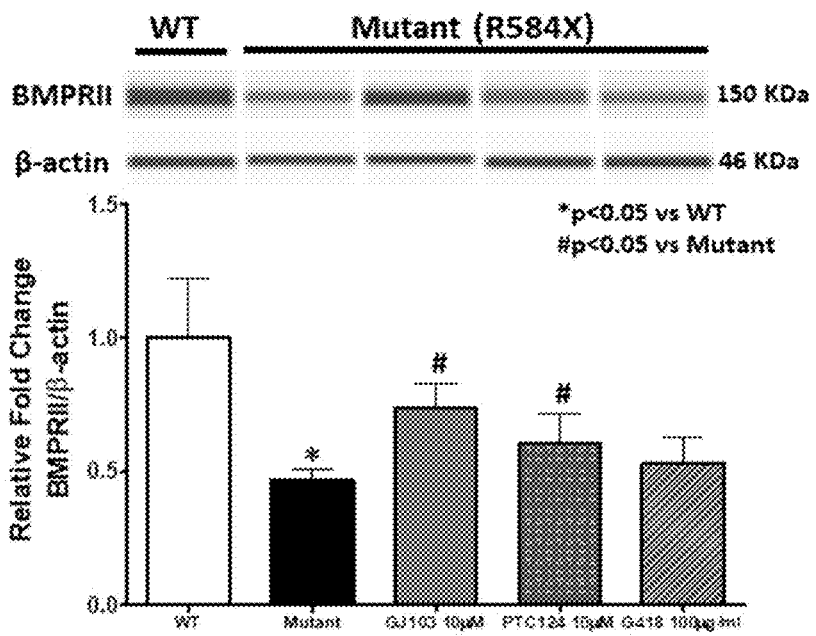
FIG. 2 shows that GJ103 induced roughly half normal or more BMPR2 protein expression levels in BOECs from a patient with hPAH harboring a nonsense mutation (R584X) in the Bmpr2 gene (N=3; Representative Western Blots are shown).
Figure 3:
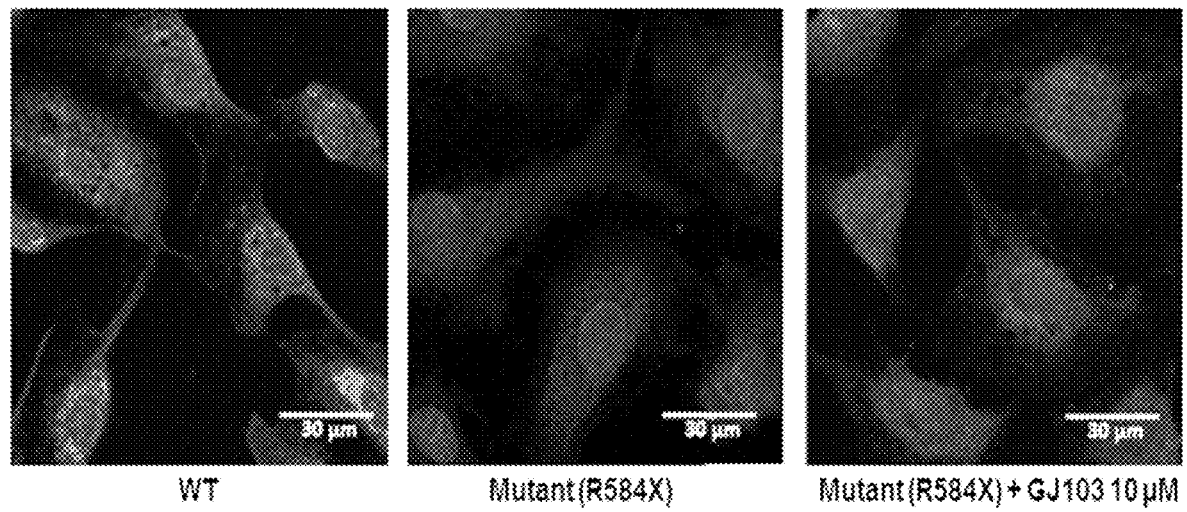
FIG. 3 shows that GJ103 induced BMPR2 protein expression. BOECs from a patient with hPAH harboring a nonsense mutation (R584X) in the Bmpr2 gene expressed markedly reduced BMPR2 protein levels, which was greatly enhanced with GJ103 treatment (N=3; Representative immunofluorescence staining is shown).

Positive controls were BOECs obtained from non-affected control individuals. Negative controls were untreated mutant cells. Compared with WT control cells, untreated mutant cells showed significantly reduced BMPR2 mRNA and protein levels. Following treatment of mutant cells with GJ103 and PTC-124 (to a much lesser degree), but not G418, this exampole observed enhanced BMPR2 mRNA and protein levels using qRT-PCR and Western blot analysis, respectively. Data on BOECs bearing the R584X mutation are shown in FIGS. 1 and 2. Reduced BMPR2 protein expression in R584 mutants (vs. WT controls) and increase in BMPR2 protein levels on GJ103 treatment was corroborated using immunofluorescence staining (FIG. 3).

Example 2. GJ103 Increased Levels of BMPR2 Downstream Targets, Indicating the Receptor and Downstream BMP Signaling is Functionally Active Having observed increased BMPR2 mRNA and protein levels on treatment of human BMPR2 mutant cells with GJ103, this example sought to determine whether GJ103-induced increases in BMPR2 protein levels is associated with active BMP signaling and induction of its downstream gene targets.

Figure 4:
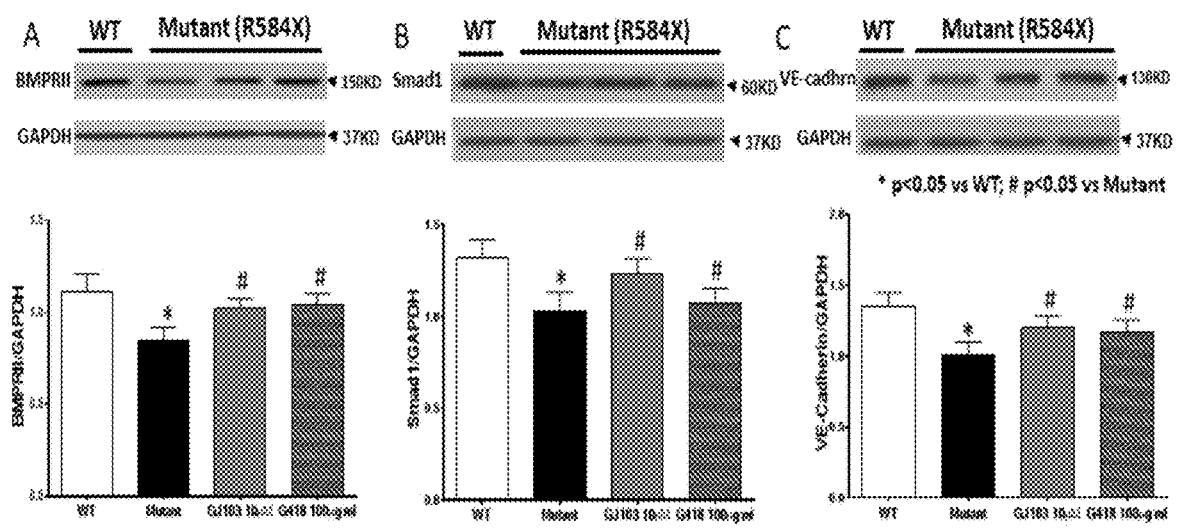
FIG. 4 shows that GJ103 normalized BMPR2 protein levels in BOECs from a patient with hPAH with R584X mutation in the Bmpr2 gene, along with the normalization of Smad1/5 and VE-cadherin, important downstream targets of BMP signaling (N=3; Representative Western blots are shown).

In theory, it is possible that BMPR2 is expressed, but is non-functional. This can occur for several reasons, such as misfolding of the protein, or dysfunctional trafficking to the cell surface. In a pleasant surprise, this example observed that GJ103 treatment of BOECs (isolated from a patient with hPAH harboring the R584X mutation) induced near normal protein expression of BMPR2 (FIG. 4A), Smad1 (FIG. 4B), a BMP signaling intermediate, and VE-cadherin (FIG. 4C), a gene readout of activation of BMP signaling. Note only a ~25% reduction in BMPR2 protein levels (vs. almost 50% reduction shown in FIG. 2) in untreated mutant control vs. WT positive control cells (FIG. 4A), suggesting wide variability in molecular phenotype, which is consistent with clinical variability in human hPAH patients harboring the same nonsense mutation (R584X).

This example therefore demonstrates that GJ103 produced significant amounts of functionally active BMPR2 protein in cells derived from clinical hPAH subjects.

Example 3. GJ103 Restored Endothelial Permeability

Loss of endothelial BMPR2 signaling is associated with compromised vascular integrity and exacerbation of inflammation-induced vascular permeability. This example sought to determine whether GJ103 can partially or fully normalize this functional response.

Figure 5:
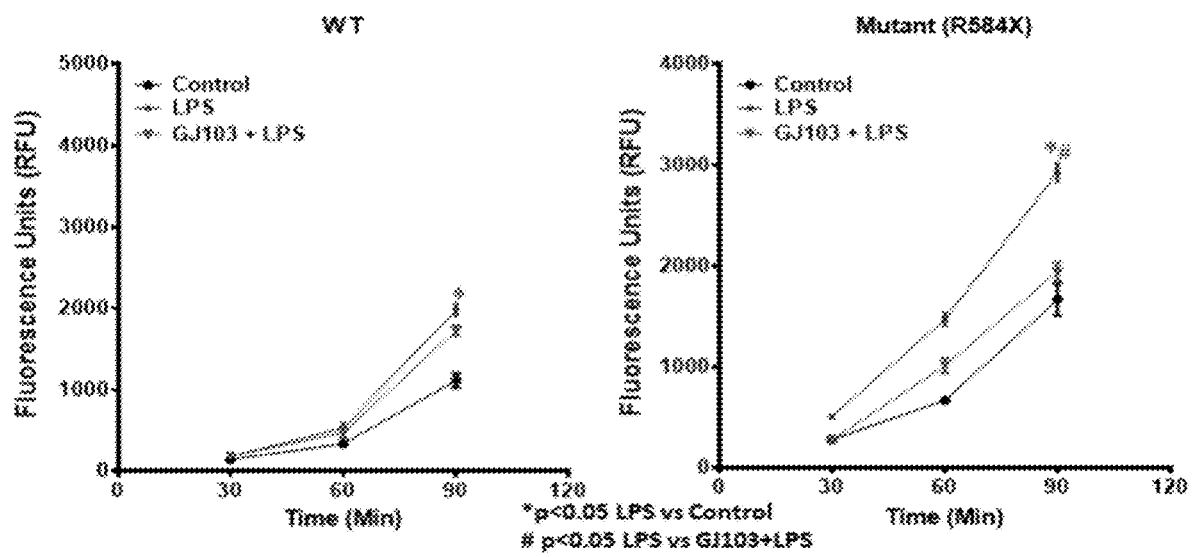
FIG. 5 shows that GJ103 demonstrated a trend towards blockage of LPS-induced increase in endothelial cell vascular permeability in R584X mutant BOEC obtained from a patient with hPAH, but not affected in WT endothelial cells (N=4 in triplicates) (*$p<0.05$ vs. LPS group).

The effect of GJ103 on the LPS-induced increase in vascular permeability was tested in both WT control and R584X mutant cells (FIG. 5). GJ103 showed a trend towards amelioration of LPS-induced increase in vascular permeability in mutant cells, but had no effect in WT cells, indicating specificity of GJ103 effect on cells bearing a nonsense mutation. As with the experiments in Examples 1-2, these data again show that GJ103 not only induces protein translation, but that the BMPR2 protein will be functional as well.

Example 4. In Vivo Safety Testing

Following the above in vitro data, this example proceeded to test in vivo safety and efficacy of GJ103.

Both acute (a single dose of GJ103 administration) and chronic (4 weekly doses of GJ103 administration) in vivo toxicity studies were performed.

Acute Safety/Toxicity. The acute safety/toxicity of GJ103 study involved 3-month old WT (C57BL/6J) mice (N=30). Mice were administered GJ103 intraperitoneally (i.p.) at doses of 10, 25, 50 or 250 mg/kg (N=5 per group) and sacrificed 1 week later. Untreated or vehicle treated mice served as controls. GJ103 treated mice did not show any overt signs of toxicity (feeding, behavioral changes, changes in body weight, and breathing). VetScan Comprehensive Diagnostic profile, and HM5 hematology systems (Abaxis, Inc) were used to perform complete blood count, basal metabolic profile (serum electrolytes and glucose), liver [total protein, albumin, globulin, total bilirubin, serum alanine aminotransferase (ALT), serum aspartate transferase (AST), alkaline phosphatase (ALP), and serum amylase (AMY)], renal [blood urea nitrogen (BUN), and creatinine (CRE)], and lipid panels (cholesterol and triglyceride). These pilot toxicology experiments produced no evidence of significant toxicity (Table 1).

Chronic Safety/Toxicity.

Mice (N=5 per group) were injected once a week for 4 weeks i.p. at doses of 25 or 50 mg/kg of GJ103, animals were sacrificed 1 week after the last injection, and the CBC and chemistries were repeated as outlined in the acute safety/toxicity study. Untreated or vehicle treated mice served as controls. Again, this example found no significant changes in any of the parameters determined (Table 2). This example also assessed LDH levels in lung, liver, kidney and heart tissue lysates in both the acute and chronic studies, but found no statistically significant differences between GJ103 treated mice and either untreated or vehicle treated controls.

TABLE 1

Blood biochemistry profile a week following one dose of GJ103

| Treatment Group | BUN mg/dL | CRE mg/dL | Cholesterol mg/dL | Triglyceride mg/dL | NA+ mM | PHOS mg/dL | CA+ mg/dL | GLU mg/dL |
|---|---|---|---|---|---|---|---|---|
| Untreated | 26 ± 3.11 | 0.3 ± 0.06 | <100 | 83 ± 3.21 | 150 ± 2.60 | 6.2 ± 0.45 | 10.3 ± 0.48 | 168 ± 7.99 |
| Vehicle | 24 ± 2.31 | 0.4 ± 0.07 | <100 | 79 ± 6.78 | 153 ± 4.58 | 7.4 ± 0.42 | 10.1 ± 1.11 | 161 ± 13.20 |
| GJ103 10 mg/kg | 27 ± 2.51 | 0.3 ± 0.05 | <100 | 79 ± 6.78 | 149 ± 1.48 | 7.4 ± 1.36 | 9.9 ± 0.82 | 155 ± 13.1 |
| GJ103 25 mg/kg | 19 ± 3.79 | 0.3 ± 0.07 | <100 | 71 ± 8.80 | 151 ± 1.73 | 7.5 ± 0.35 | 10.5 ± 0.59 | 134 ± 4.58 |
| GJ103 50 mg/kg | 20 ± 1.53 | 0.2 ± 0.06 | <100 | 79 ± 7.30 | 149 ± 2.00 | 8.4 ± 0.92 | 10.0 ± 0.35 | 184 ± 30.27 |
| GJ103 250 mg/kg | 24 ± 2.31 | 0.3 ± 0.07 | <100 | 66 ± 9.57 | 149 ± 3.00 | 8.1 ± 2.48 | 10.6 ± 0.60 | 191 ± 63.58 |

| Treatment Group | TP g/dL | ALB g/dL | ALP g/dL | ALT g/dL | TBIL mg/dL | GLOB mM | AMY mg/dL |
|---|---|---|---|---|---|---|---|
| Untreated | 5.7 ± 0.29 | 4.2 ± 0.18 | 55 ± 12.43 | 31 ± 3.13 | 0.3 ± 0.05 | 1.5 ± 0.30 | 728 ± 30.36 |
| Vehicle | 5.7 ± 0.00 | 4.2 ± 0.1 | 57 ± 22.41 | 25 ± 4.16 | 0.2 ± 0.00 | 1.5 ± 0.06 | 647 ± 50.93 |
| GJ103 10 mg/kg | 5.1 ± 0.66 | 4.1 ± 0.37 | 47 ± 12.14 | 29 ± 5.13 | 0.2 ± 0.00 | 1.5 ± 0.49 | 720 ± 41.44 |
| GJ103 25 mg/kg | 5.7 ± 0.12 | 4.0 ± 0.30 | 42 ± 27.15 | 24 ± 2.12 | 0.2 ± 0.06 | 1.6 ± 0.31 | 833 ± 73.45 |
| GJ103 50 mg/kg | 5.4 ± 0.23 | 4.1 ± 0.30 | 56 ± 22.14 | 30 ± 2.83 | 0.2 ± 0.06 | 1.2 ± 0.12 | 796 ± 129.65 |
| GJ103 250 mg/kg | 5.7 ± 0.26 | 4.4 ± 0.21 | 43 ± 10.54 | 34 ± 7.07 | 0.3 ± 0.00 | 1.4 ± 0.06 | 1178 ± 480.67 |

TABLE 2

Blood biochemistry 1 week following 4 weekly GJ103 injections

| Treatment Group | BUN mg/dL | CRE mg/dL | Cholesterol mg/dL | Triglyceride mg/dL | NA+ mM | PHOS mg/dL | CA+ mg/dL | GLU mg/dL |
|---|---|---|---|---|---|---|---|---|
| Untreated | 25 ± 3.06 | 0.3 ± 0.06 | <100 | 90 ± 4.27 | 149 ± 1.00 | 6.6 ± 0.78 | 10.0 ± 0.21 | 167 ± 17.16 |
| Vehicle | 23 ± 3.79 | 0.4 ± 0.15 | <100 | 73 ± 8.45 | 149 ± 1.53 | 6.5 ± 0.15 | 9.7 ± 0.06 | 180 ± 12.7 |
| GJ103 25 mg/kg | 19 ± 3.05 | 0.3 ± 0.08 | <100 | 62 ± 10.6 | 149 ± 3.19 | 6.7 ± 0.99 | 9.9 ± 0.4 | 173 ± 19.14 |
| GJ103 50 mg/kg | 20 ± 3.40 | 0.3 ± 0.06 | <100 | 61 ± 13.38 | 149 ± 2.50 | 7.1 ± 1.95 | 9.9 ± 0.54 | 176 ± 15.52 |

| Treatment Group | TP g/dL | ALB g/dL | ALP g/dL | ALT g/dL | TIM mg/dL | GLOB mM | AMY mg/dL |
|---|---|---|---|---|---|---|---|
| Untreated | 5.6 ± 0.06 | 4.2 ± 0.15 | 78 ± 10.07 | 27 ± 1.73 | 0.2 ± 0.06 | 1.4 ± 0.10 | 726 ± 44.56 |
| Vehicle | 5.4 ± 0.06 | 4.0 ± 0.15 | 83 ± 2.65 | 27 ± 0.58 | 0.2 ± 0.06 | 1.4 ± 0.06 | 680 ± 81.99 |
| GJ103 25 mg/kg | 5.7 ± 0.18 | 4.2 ± 0.27 | 69 ± 17.52 | 27 ± 4.38 | 0.2 ± 0.04 | 1.8 ± 0.88 | 605 ± 72.39 |
| GJ103 50 mg/kg | 5.6 ± 0.39 | 4.1 ± 0.36 | 71 ± 13.00 | 30 ± 12.48 | 0.2 ± 0.05 | 1.5 ± 0.38 | 742 ± 101.74 |

Example 5. In Vivo Efficacy Testing

Figure 6:
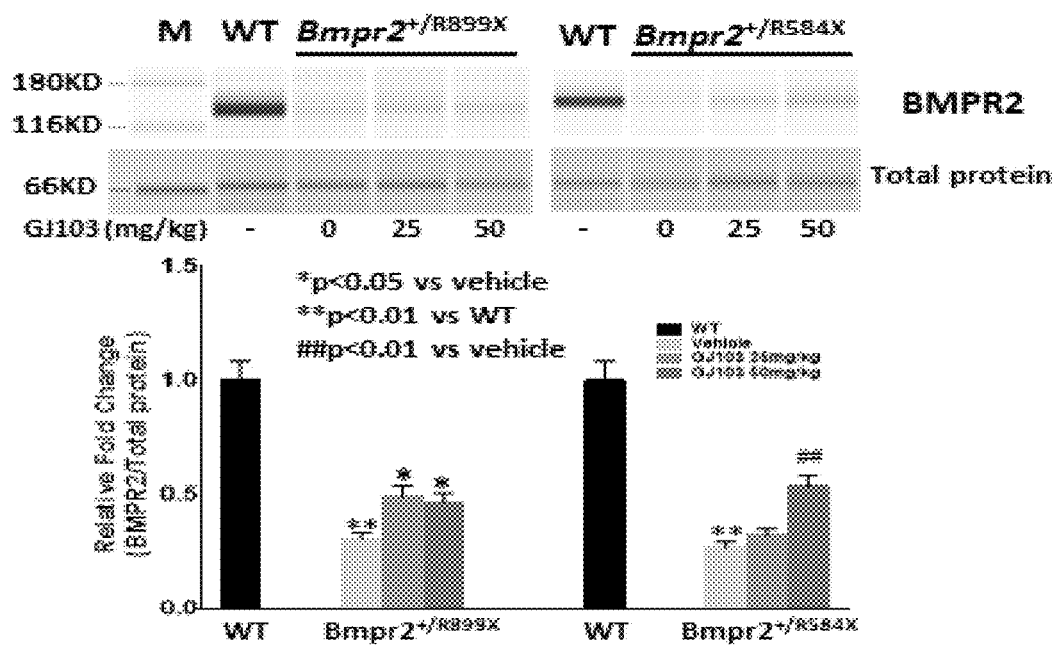
FIG. 6 shows that lung homogenates of Bmpr2+/R899X and Bmpr2+/R584X mice expressed ~25-33% BMPR2 protein vs. untreated WT (Bmpr2+/+) littermate controls. GJ103 administered once daily x 5 significantly increased BMPR2 expression in lung homogenates vs. controls. Total protein and loading control is shown (N=4); Representative Western blots are shown.

Having determined apparent in vivo safety of GJ103, this example next assessed if GJ103 administered i.p. improves BMPR2 proteins levels and activates BMP signaling in the pulmonary arteries of mice with a nonsense mutation. This example shows that GJ103 induced in vivo expression of BMPR2 in the lungs of $Bmpr2^{+/R899X}$ and $Bmpr2^{+/R584X}$ mice To test this, $Bmpr2^{+/R899X}$ and $Bmpr2^{+/R584X}$ mice were administered vehicle, 25 mg/kg or 50 mg/kg GJ103 i.p. once daily for 5 days. Mice were then sacrificed and lung homogenates probed for BMPR2 protein levels (FIG. 6). Compared to WT (Bmpr2+/+) littermate controls, both $Bmpr2^{+/R899X}$ and $Bmpr2^{+/R584X}$ mice expressed ~25-33% of WT BMPR2 protein levels. It therefore shows that GJ103 significantly increased BMPR2 expression vs. untreated controls to levels that could potentially prevent or normalize the hPAH phenotype.

This example next tested the function of GJ103-induced expression of BMPR2 protein using an in vivo LPS vascular permeability assay and Evans blue dye as a marker of vascular leakage and showed that GJ103 restored LPS-induced Increase in pulmonary vascular/endothelial permeability in vivo in $Bmpr2^{+/R899X}$ mice.

Figure 7:
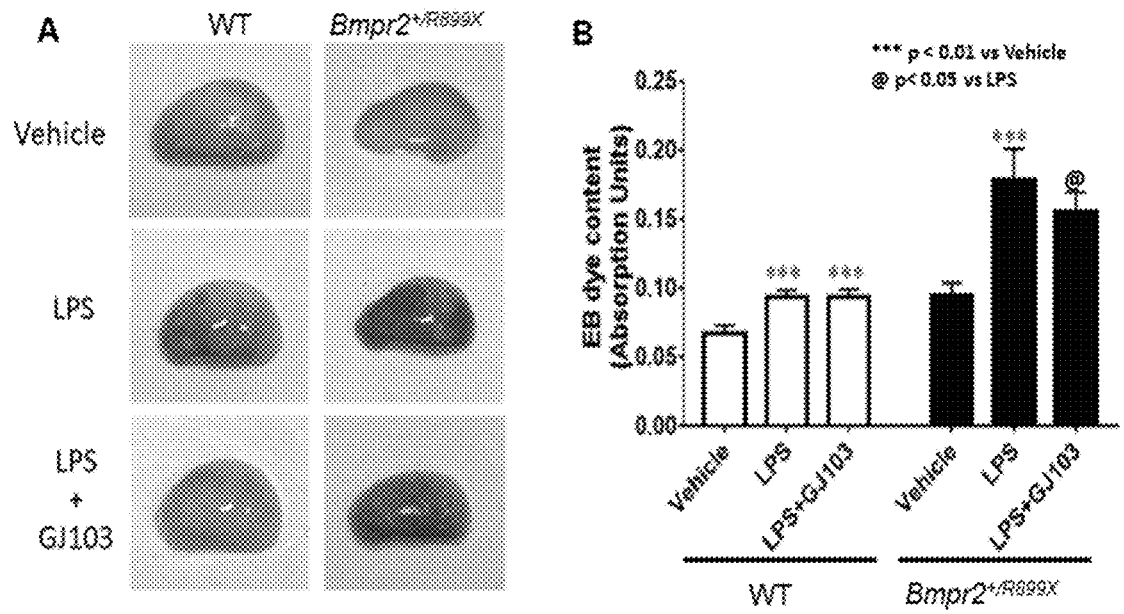
FIG. 7 shows that GJ103 restores in vivo LPS-induced increase in vascular/endothelial permeability in Bmpr2+/R899X mice but not WT controls. Images of lungs isolated from mice injected with 4 mg/kg LPS or vehicle and GJ103 (50 mg/kg) 22 hours prior to Evans blue dye injection (all injected i.p.), which was delivered 2 hours prior to sacrifice are shown (A). Quantitative assessment of extravascular Evans blue dye in the lungs of the mice are shown (B); N=2, 4 lungs for each condition).

$Bmpr2^{+/R899X}$ and WT mice injected with LPS developed pulmonary vascular leakage (FIG. 7A), which was quantified by extravasation of Evans blue dye into lung tissue (FIG. 7B). $Bmpr2^{+/R899X}$ mice demonstrated much greater increase in dye extravasation compared to WT littermates, but this was significantly blocked with GJ103 (50 mg/kg). There was no effect of GJ103 on LPS-induced leakage in WT controls. Collectively, these findings are consistent with the interpretation that BMPR2 protein induced by treatment with GJ103 in $Bmpr2^{+/R899X}$ mice was functionally active. Based on this finding, it is contemplated that GJ103-induced expression of BMPR2 can slow or prevent development of hPAH pathology.

Figure 8:
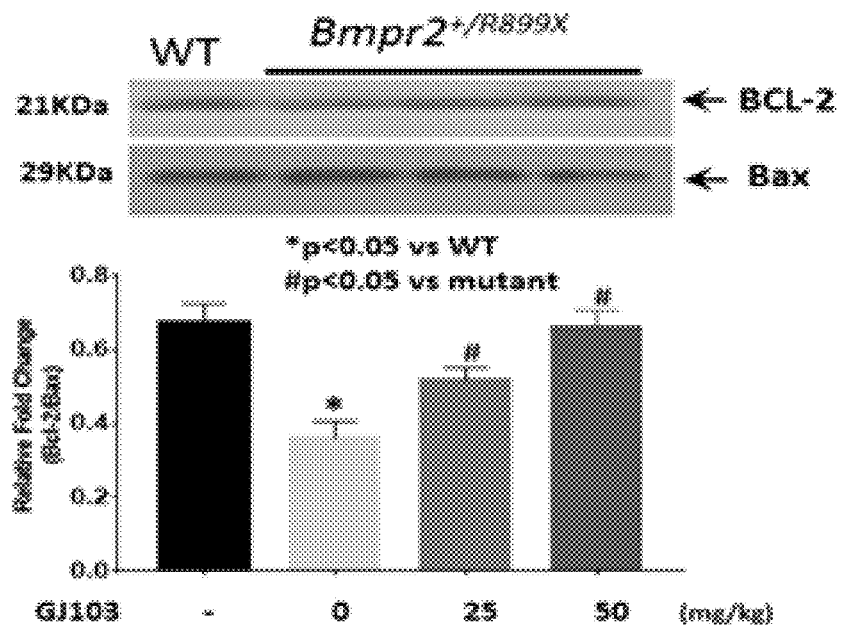
FIG. 8 shows that GJ103 blocked increased lung apoptosis in Bmpr2+/R899X mice. Lung apoptosis, as determined by BCL-2/Bax ratio in lung homogenates of Bmpr2+/R899X and WT control mice showed increased apoptosis in Bmpr2 mutant mice, which was dose-dependently blocked with GJ103 (N=3); Representative Western blots are shown.

Pulmonary endothelial cell apoptosis is thought to initiate development of hPAH by triggering vaso-occlusive fibroproliferation. Therefore, this example next determined the effect of GJ103 on BCL-2 and Bax lung protein levels in WT and $Bmpr2^{+/R899X}$ mice, and assessed how GJ103 affects spontaneous apoptosis in $Bmpr2^{+/R899X}$ mice lungs. Consistent with GJ103's effects on BMPR2 expression (FIGS. 1-4 and 6) as well as the restoration of endothelial cell integrity (FIGS. 5 and 7), GJ103 also blocked spontaneous apoptosis in $Bmpr2^{+/R899X}$ mice lungs (FIG. 8).

The above examples, in summary, demonstrate that, in an appropriate mouse model of hPAH developed herein, a lead SMRT compound candidate (GJ103) has been identified. GJ103 is water soluble, readily administered, and reads through all three clinically relevant nonsense mutations to produce significant amounts of BMPR2 protein. GJ103 induces increased expression of BMP pathway signaling intermediates (Smads) and downstream gene targets (Idl and VE-cadherin) of BMPR2-mediated signaling, indicating that BMPR2 protein is indeed functional. GJ103 induces translation of significant quantities of BMPR2 protein in human BOECs obtained from patients with hPAH caused by nonsense mutations in the BMPR2 gene, thus establishing clinical relevance. GJ103 restores endothelial permeability in vitro in an LPS-induced functional assay and shows no evidence of toxicity thus far at doses that produce in vivo readthrough. Moreover, GJ103 induces expression of significant BMPR2 protein in the lungs of Bmpr2$^{+/R899X}$ and Bmpr2$^{+/R584X}$ mice, partially blunts LPS-induced increases in endothelial permeability, and blocks lung apoptosis, which is also consistent with GJ103-induced expression of functionally active BMPR2 protein.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method for treating, preventing, or slowing the rate of development of heritable pulmonary artery hypertension (hPAH) in a subject in need thereof, wherein the hPAH is mediated by a nonsense mutation in the bone morphogenetic protein receptor type II (Bmpr2), selected from the group consisting of R584X, R321X, R899X and combinations thereof, wherein the method comprises administering to the subject a compound of Formula Ia:

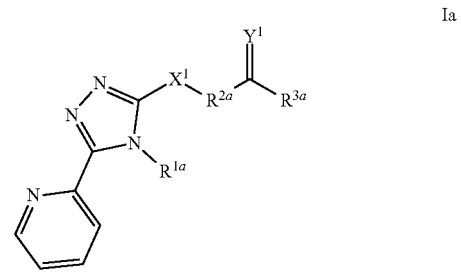

Ia or a pharmaceutically acceptable salt, wherein:

R$^{1a}$ is 2-hydroxylphenyl, 2-alkoxyphenyl, 3-hydroxylphenyl, or 3-alkoxyphenyl;

X$^1$ is S, O, NH, or N(C$_{1-3}$-alkyl);

R$^{2a}$ is (CH$_2$)$_m$;

m is 1, 2, or 3;

Y$^1$ is O, S, or NH;

R$^{3a}$ is hydroxy or —NR$^7$R$^{7a}$;

R$^7$ is hydrogen or C$_{1-3}$-alkyl;

R$^{7a}$ is hydroxyalkyl; phenyl substituted with 1, 2, or 3 R$^8$ groups; phenyl substituted with two independently selected halo; and each R$^8$ is independently hydroxy or haloalkyl; and provided that 1) when X$^1$ is S, R$^{2a}$ is —CH$_2$—, Y$^1$ is O, and R$^{3a}$ is —NR$^7$R$^{7a}$ and R$^7$ is hydrogen, then R$^{7a}$ is not 2-methoxyphenyl; and 2) when R$^{1a}$ is 2-methoxyphenyl, X$^1$ is S, R$^{2a}$ is —CH$_2$—, Y$^1$ is O, and R$^{3a}$ is —NR$^7$R$^{7a}$ and R$^7$ is hydrogen, then R$^{7a}$ is not 4-methoxyphenyl.

2. The method of claim 1, wherein the compound is of formula:

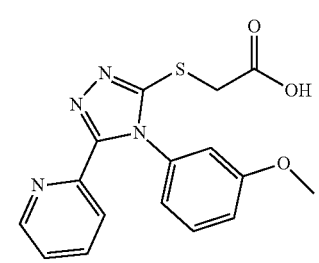

or a pharmaceutically acceptable salt thereof.

3. The method of claim 2, wherein the compound is

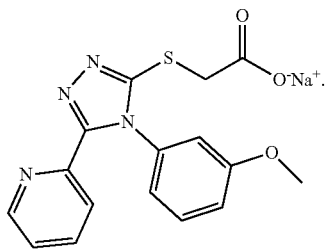

4. The method of claim 1, further comprising administering to the subject an effective amount of a drug selected from the group consisting of ambrisentan, bocentan, macitentan, riociguat, selexipag, sildenafil, tadalafil, treprostinil, Iloprost tromethamine, treprostinil, epopostenol sodium, treprostinil and combinations thereof.

5. The method of claim 1, further comprising administering to the subject an effective amount of a nonsense-mediated decay inhibitor (NMDI).

6. The method of claim 1, wherein the nonsense mutation is R584X.

7. The method of claim 1, wherein the nonsense mutation is R321X.

8. The method of claim 1, wherein the nonsense mutation is R899X.

9. The method of claim 1, wherein the administration is oral.

10. The method of claim 1, wherein the administration is by injection.

11. The method of claim 1, wherein the administration is by inhalation.

* * * * *